United States Patent
Steur

(10) Patent No.: US 9,526,597 B2
(45) Date of Patent: Dec. 27, 2016

(54) MOUTHPIECE FOR BRUSHING TEETH

(75) Inventor: Jelte Steur, Zwolle (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1150 days.

(21) Appl. No.: 12/994,943

(22) PCT Filed: May 27, 2009

(86) PCT No.: PCT/IB2009/052239
§ 371 (c)(1),
(2), (4) Date: Nov. 29, 2010

(87) PCT Pub. No.: WO2009/150559
PCT Pub. Date: Dec. 17, 2009

(65) Prior Publication Data
US 2011/0072605 A1    Mar. 31, 2011

Related U.S. Application Data

(60) Provisional application No. 61/060,349, filed on Jun. 10, 2008.

(51) Int. Cl.
*A61C 17/22* (2006.01)
*A61C 17/34* (2006.01)

(52) U.S. Cl.
CPC ........... *A61C 17/222* (2013.01); *A61C 17/228* (2013.01); *A61C 17/3481* (2013.01); *A61C 17/22* (2013.01)

(58) Field of Classification Search
CPC .. A61C 17/222; A61C 17/3481; A61C 17/228
USPC ............ 15/105, 167.1, 167.2; 601/129
See application file for complete search history.

(56) References Cited

U.S. PATENT DOCUMENTS

| | | | |
|---|---|---|---|
| 4,224,710 A * | 9/1980 | Solow | 15/22.1 |
| 5,177,827 A * | 1/1993 | Ellison | 15/22.1 |
| 5,337,435 A * | 8/1994 | Krasner et al. | 15/23 |
| 5,365,624 A | 11/1994 | Berns | |
| 5,460,186 A | 10/1995 | Buchhold | |
| 5,523,745 A | 6/1996 | Fortune et al. | |
| 6,353,956 B1 * | 3/2002 | Berge | 15/22.1 |
| 7,044,737 B2 | 5/2006 | Fu | |
| 7,481,773 B1 * | 1/2009 | Dorroh et al. | 600/549 |

(Continued)

FOREIGN PATENT DOCUMENTS

| | | |
|---|---|---|
| GB | 2163641 A | 3/1986 |
| JP | S6164245 A | 4/1986 |

(Continued)

OTHER PUBLICATIONS

Chris Salem et al; "An Isometric Tongue Pointing Device", Technical Notes, CHI. 97, Atlanta, GA. Mar. 22-27, 1997.

(Continued)

*Primary Examiner* — Michael Jennings

(57) ABSTRACT

The mouthpiece includes a mouthpiece body (10) having portions (12, 14) configured to receive the user's upper and lower sets of teeth when it is inserted into the user's mouth. Mounted in the receiving portions are teeth-cleaning assemblies (16) which include bristles for cleaning of the teeth and a system for moving the bristles against the teeth to scrub and clean the teeth. Control elements (22) for the cleaning assemblies are actuated by a selected interior portion or element of the user's mouth, such as the tongue, cheek, lips or jaw.

15 Claims, 3 Drawing Sheets

(56) References Cited

U.S. PATENT DOCUMENTS

2007/0259310 A1    11/2007    Goodson et al.
2009/0229062 A1*    9/2009    Filby ............................ 15/22.1

FOREIGN PATENT DOCUMENTS

| JP | H0495730 U | 8/1992 |
|---|---|---|
| JP | 2003180718 | 7/2003 |
| JP | 2005251138 A | 9/2005 |
| WO | 2005107638 A1 | 11/2005 |
| WO | 2007072430 A2 | 6/2007 |

OTHER PUBLICATIONS

Solomon et al: "The Effect of Jaw Position on Measures of Tongue Strength and Endurance"; J. Speech Lang Hear Res. Jun. 2004, vol. 47 (3), pp. 584-594.
Tang et al: "Tactile Sensitivity of the Tongue on Photo-Lithographically Fabricated Patterns"; Proceedings of the First Joint BMES/EMBS Conference, Atlanta, GA, 1999, p. 63.
Tang et al: "An Oral Tactile Interface for Blind Navigation"; IEEE Transactions on Neural Systems and Rehabilitation Engineering, vol. 14, No. 1, Mar. 2006, pp. 116-123.

* cited by examiner

MOUTHPIECE FOR BRUSHING TEETH

This invention relates generally to mouthpieces, and more specifically to mouthpieces which accomplish teeth cleaning.

Typically, oral health care involving cleaning of the teeth is accomplished by toothbrushes, either manual or power, which are inserted into the mouth by the user and guided from region to region of the mouth. Toothbrushes have varying degrees of success for cleaning; power toothbrushes are generally more effective than manual. The effectiveness, however, of all toothbrushes depends to a significant extent on the skill and patience of the user.

Teeth cleaning can also be carried out by the use of a mouthpiece which is inserted into the mouth, typically connected to a control member positioned outside the mouth. In some cases, the device can be controlled by inserting finger(s) into the mouth to contact controls on the mouthpiece, although this can be messy, uncomfortable and hence disadvantageous.

Accordingly, it is desirable to have a mouthpiece which is capable of cleaning teeth, typically all at once, without the need for any manual effort or involvement on the part of the user, either for control or manipulation of the mouthpiece.

Accordingly, disclosed herein is a mouthpiece for cleaning of teeth, comprising: a mouthpiece body configured to receive at least a region of a user's set of teeth when the mouthpiece body is inserted into the mouth; a teeth cleaning assembly, positioned in the mouthpiece body, including bristles and a system for moving the bristles against the teeth to clean the teeth; and a control assembly, activated by a selected interior portion or element of the user's mouth, for controlling the teeth cleaning assembly.

Figure 1:
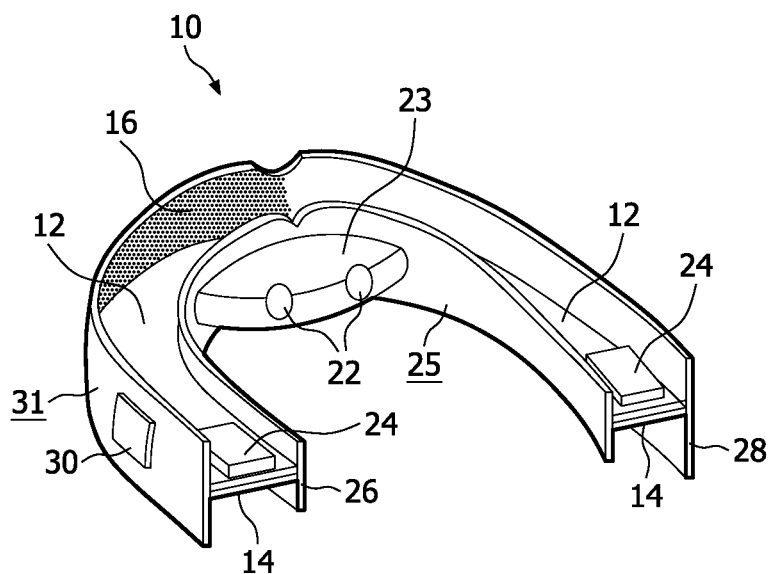
FIG. 1 shows a perspective view of a teeth-cleaning mouthpiece having several different control members.
Figure 2:
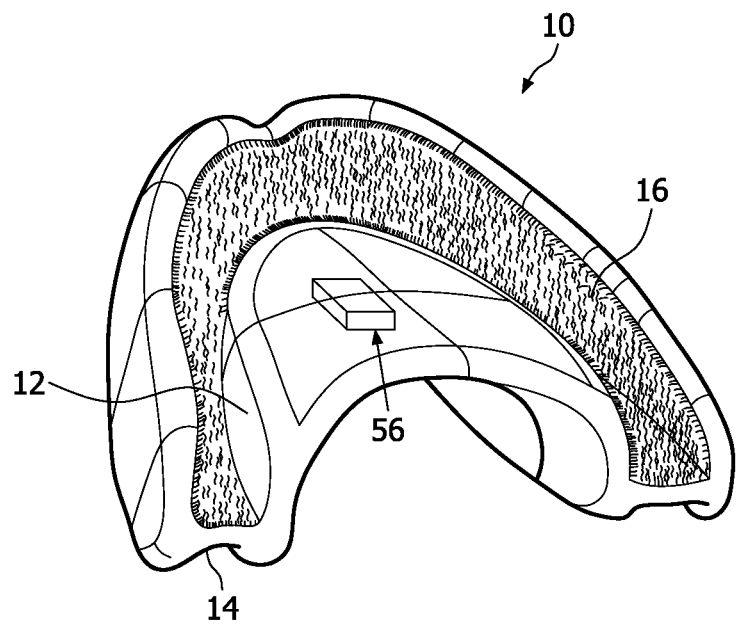
FIG. 2 is a perspective view of a teeth-cleaning mouthpiece with a microprocessor control, and showing bristles used for cleaning teeth.

FIGS. 1 and 2 show a mouthpiece 10 which is generally configured to fit conveniently within the mouth of the user. Mouthpiece 10 in the embodiment shown includes upper and lower teeth-receiving portions 12 and 14 which are configured, respectively, to receive all the teeth in both the upper and lower jaws. However, it should be understood that other embodiments could have configurations which receive only a portion of the teeth within the mouth, such as just the front and adjacent teeth on the upper and/or lower jaws, or other regions. Positioned within the teeth-receiving portions are teeth cleaning assemblies, which include conventional bristle sets, referred to as a whole at 16, wherein the bristles can be any one of a variety of available bristles effective for cleaning teeth, including, for instance, nylon bristles of appropriate length and diameter for a teeth cleaning mouthpiece. The bristles 16 are hence generally arranged and configured to produce cleaning of the teeth surfaces.

Furthermore, the teeth-receiving portions and the bristles positioned therein are arranged so that when the mouthpiece is fully inserted into the mouth, the bristles contact all or a selected portion of the teeth and then in operation are moved, as discussed in more detail below, to produce a scrubbing effect on the teeth. It should be understood that the bristle arrangement can vary significantly, from a set of fixed, individual bristles/bristle tufts which in total cover all the surfaces of the teeth, to a compact bristle head, capable of moving in the mouthpiece at the control of the user to contact all of the teeth over a selected brushing time.

FIG. 1 shows various control members for the mouthpiece. Control features include on/off control, as well as control of the frequency or amplitude of the bristle action. One control arrangement is designed to be activated by the tongue of the user, operating on buttons 22 which are located in a mounting element 23 secured to the interior surface 25 of the mouthpiece. The tip of the tongue is quite dexterous and can move forward, backward, up, down and sideways to operate buttons 22 or similar elements. One button 22 can control the on/off status of the mouthpiece, while another button can control frequency or magnitude of the bristle action. The pressure that can be exerted by the tongue on the buttons depends upon how far the mouthpiece forces the jaw to open. The pressure which can be exerted by the tongue ranges from 50-80 kPa for a closed jaw and 26-44 kPa for an open jaw. Buttons are available which can respond to such a range of pressure. In addition to buttons, compression switches, touch sensors, pressure sensors, toggle switches or even rocker switches can be used.

Figure 8:
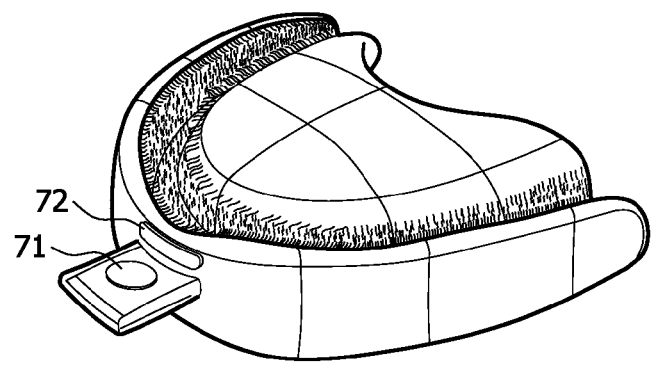
FIG. 8 is a perspective view of a mouthpiece having another control arrangement.

Referring still to FIG. 1, the jaws of the user can be used to operate buttons 24-24 located at the rear ends 26, 28 of the mouthpiece. Control of the mouthpiece operation can also be accomplished by cheek action to impact buttons 30 positioned along the side surfaces 31 of the mouthpiece, usually near the rear ends 26, 28 of the mouthpiece. Movement of the cheeks, with some practice, can be sufficient to operate conventional buttons. In addition to the use of the above portions/elements of the mouth to operate the mouthpiece, other movements, such as a head shake, can also be used. For shaking of the head, an accelerometer can be used to control operation of the mouthpiece. The lips can also be used to exert a force on a control member. FIG. 8 shows a mouthpiece 70 with control members 71 and 72 which are responsive to lip action.

Figure 3:
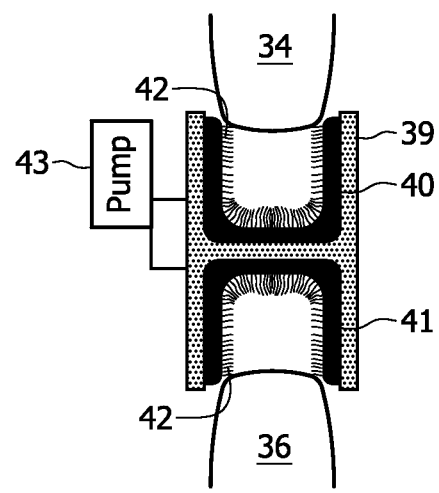
FIG. 3 is a cross-sectional view of one teeth-cleaning assembly for the mouthpiece of FIG. 1.

One arrangement for carrying out actual brushing of the teeth with the mouthpiece is shown in FIG. 3. Upper and lower teeth 34 and 36 are shown in a mouthpiece operatively positioned in the mouth of the user. The mouthpiece structure, which is typically a durable plastic material, is shown at 39. Bellows elements 40, 41 are positioned adjacent the surfaces of the teeth-receiving portions of the mouthpiece. Bristles 42 are attached to the respective bellows elements 40, 41. Changing the pressure in the bellows element 40, 41, such as by a pump 43, results in movement of the bellows toward and away from the teeth. As a result, the bristles 42 also move against the teeth and then away from the teeth, resulting in cleansing of the teeth by a scrubbing-type action.

Figures 4, 5:
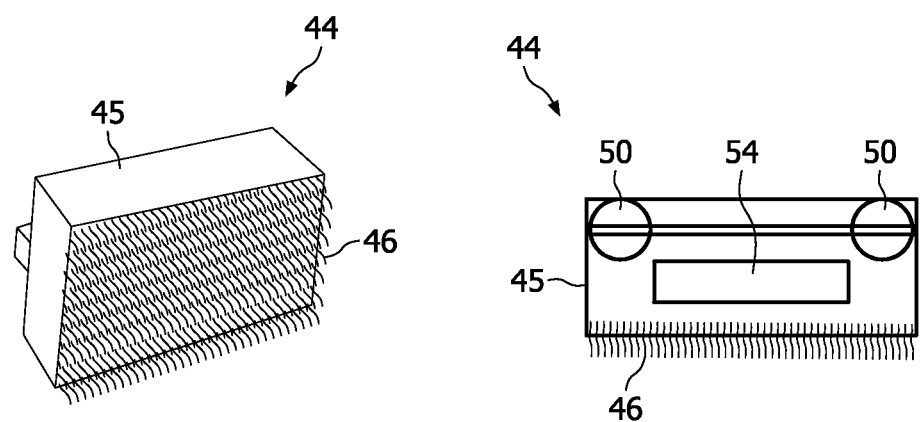
FIGS. 4 and 5 are perspective and top views of another teeth-cleaning assembly.
Figure 6:
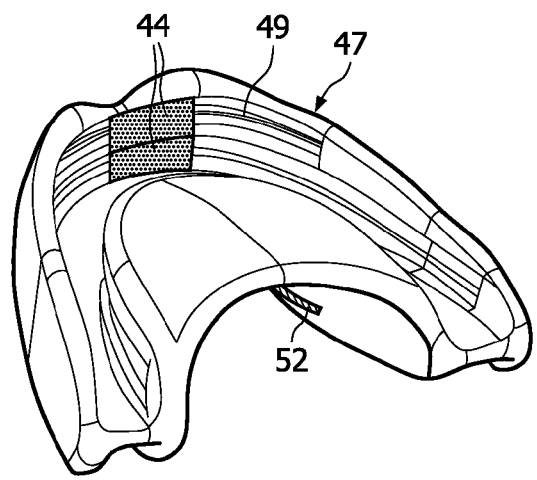
FIG. 6 is a perspective view of the teeth-cleaning assembly of FIGS. 4 and 5 in position in a mouthpiece.

Another arrangement is shown in FIGS. 4-6. In this arrangement, multiple cleaning head assemblies 44-44 are movably positioned in the teeth-receiving portions of a mouthpiece 47. Each cleaning head assembly 44 (FIG. 4) includes a small housing 45 with bristles 46 mounted thereto. Each cleaning head assembly also includes a pair of wheels 50-50 (FIG. 5) which enable the head to move along a track 49 in the teeth-receiving portions. The cleaning head assembly is driven by a vibrator 54 similar to that used in cell phones. The vibration of the bristles against the teeth results in cleansing of the teeth. The position of the cleaning head assembly can be controlled by a piezoelectric driver or a small linear actuator. The tongue can engage a control assembly 52 to steer the cleaning head to desired locations along the mouthpiece.

It should be understood that there can be other specific brushing arrangements in a mouthpiece which produce cleansing of the teeth.

In addition to the above, the mouthpiece could include a microprocessor 56 (FIG. 2), wherein the microprocessor memory may contain a plurality of different modes or routines involving different pressures and brushing times in order to provide specific cleansing effects. The microprocessor can also be controlled by tongue manipulation.

Hence, a mouthpiece can be specifically constructed to provide significant effective cleaning of teeth, controlled by elements/portions of the mouth structure itself, so that the mouthpiece can be kept within the mouth, without the need for manual control, such as by the fingers of a user.

Figure 7:
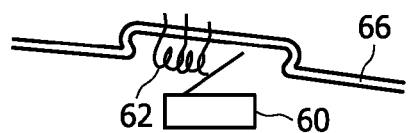
FIG. 7 is a simplified mechanical diagram showing a feedback arrangement for the mouthpiece.

Several feedback arrangements can also be used with the mouthpiece to provide the user an indication of the operational status or change in status of the mouthpiece. In one arrangement, the feedback is tactile, i.e. the user will be able to feel a difference between the two operating states of any control button, such as the buttons having two positions. In another arrangement, a point or similar element will come up when the mouthpiece is actuated. In still another arrangement, illustrated in FIG. 7, heat is used. When a button switch 60 is operated via the tongue or other mouth member, a heating coil 62 is actuated which heats a thermally conductive/electrically insulating cover 66 for the switch. The user can sense a change in temperature of the covered switch, indicating when the switch is in a particular position. It is also possible to position the coil at a different location than immediately under the switch. In still another arrangement, an electrical signal can be used for feedback. A conductive element that is in contact with the mouth can provide an electrical signal that the user can sense.

Hence, a new mouthpiece, designed to be completely carried within the mouth, is disclosed for effective cleaning of the mouth. Various cleaning arrangements can be used as well as a variety of control arrangements, including operation by various physical portions of the mouth including, for instance, the tongue.

Although a preferred embodiment of the invention has been disclosed here for the purposes of illustration, it should be understood that various changes, modifications and substitutions may be incorporated in the embodiment without departing from the spirit of the invention, which is defined by the claims which follow.

The invention claimed is:

1. A mouthpiece for cleaning of teeth, comprising:
a mouthpiece body (10) configured to receive at least a region of a user's set of teeth when the mouthpiece body is inserted into the mouth;
a teeth cleaning assembly (16), positioned in the mouthpiece body, including bristles and a system for moving the bristles against the teeth to clean the teeth; and
a hands-free control assembly (22), adapted and arranged to be activatable by a selected interior portion or element of the user's mouth, for controlling the teeth cleaning assembly.

2. The mouthpiece of claim 1, wherein the control assembly is positioned and arranged to be responsive to tongue action or lip action of the user.

3. The mouthpiece of claim 1, wherein the control assembly (30) is positioned and arranged to be responsive to a movement of the cheek of the user.

4. The mouthpiece of claim 1, wherein the control assembly (24) is positioned and arranged to be responsive to a movement of the jaw of the user.

5. The mouthpiece of claim 1, wherein the control assembly includes at least one button which is mounted in the mouthpiece body.

6. The mouthpiece of claim 1, wherein the teeth-cleaning assembly includes a bellows member (40, 41) to which the bristles are mounted and a pump (43) connected to the bellows member to move the bristles against and away from the teeth.

7. The mouthpiece of claim 1, wherein the teeth-cleaning assembly includes a cleaning head (44) which is moveable along the mouthpiece body, wherein the cleaning head includes bristles (46) and a vibrator (54) which is controlled to move the bristles against and away from the teeth.

8. The mouthpiece of claim 1, including a microprocessor (56) containing a plurality of selectable modes or routines of operation of the teeth-cleansing assembly, including different combinations of bristle pressure and time of operation.

9. The mouthpiece of claim 1, wherein the mouthpiece body is configured to receive and clean substantially all of the teeth of the user.

10. The mouthpiece of claim 1, wherein the control assembly includes a system to provide to the user feedback information on the operating status of the teeth-cleaning assembly.

11. The mouthpiece of claim 10, wherein the feedback is in the form of a temperature change of a selected portion (60, 62, 66) of the control assembly or a selected portion of the mouthpiece body or an electrical signal directed to a selected element of the user's mouth.

12. The mouthpiece of claim 10, wherein the feedback is in the form of a spatial position of one or more elements of the control assembly.

13. The mouthpiece of claim 10, wherein the feedback is in the form of a presentation of a protuberance from the mouthpiece body.

14. The mouthpiece of claim 1, wherein the control assembly includes buttons for contact by the selected interior portion or element of the user's mouth.

15. The mouthpiece of claim 1, wherein the control assembly includes contact elements selected from the following: compression switches, touch sensors, pressure sensors, toggle switches and rocker switches, for contact by the selected portion or element of the user's mouth.

* * * * *